United States Patent [19]

Drzewiecki et al.

[11] 3,952,576

[45] Apr. 27, 1976

[54] LAMINAR JET FLUID PROPERTY SENSOR

[75] Inventors: Tadeusz M. Drzewiecki, Silver Spring; Francis M. Manion, Rockville, both of Md.

[73] Assignee: The United States of America as represented by the Secretary of the Army, Washington, D.C.

[22] Filed: Apr. 10, 1975

[21] Appl. No.: 566,900

[52] U.S. Cl. .................................. 73/54; 137/833
[51] Int. Cl.² .................................... G01N 11/00
[58] Field of Search ................. 73/53, 54; 137/833

[56] References Cited
UNITED STATES PATENTS

| | | |
|---|---|---|
| 3,363,453 | 1/1968 | Erickson .......................... 73/54 |
| 3,366,143 | 1/1968 | Bauer ........................... 137/833 X |
| 3,505,855 | 4/1970 | Rolland .......................... 73/54 X |
| 3,678,733 | 7/1972 | Blatter ............................ 73/54 |

FOREIGN PATENTS OR APPLICATIONS

| | | |
|---|---|---|
| 1,130,973 | 10/1968 | United Kingdom ............. 137/833 |

*Primary Examiner*—Richard C. Queisser
*Assistant Examiner*—Joseph W. Roskos
*Attorney, Agent, or Firm*—Nathan Edelberg; Robert P. Gibson; Saul Elbaum

[57] ABSTRACT

A laminar fluidic device for sensing fluid properties that affect viscosity is disclosed, the device comprising a source of supply for directing a jet of fluid outwardly from a nozzle, a pair of control channels disposed on opposite sides of the jet of fluid for deflecting the jet in response to a difference in the resistance of one control channel with respect to the other control channel, such resistance difference effecting a pressure differential across the jet, a pair of output channels for receiving the jet of fluid in accordance with the deflection thereof, and vent means disposed between the nozzle and the output channels. Each of the control channels normally exhibits channel resistance equal to the jet edge resistance and this normal channel resistance is brought about through a preselection of the control channel length, which length is contemplated to be approximately 70 times the width of the nozzle.

4 Claims, 1 Drawing Figure

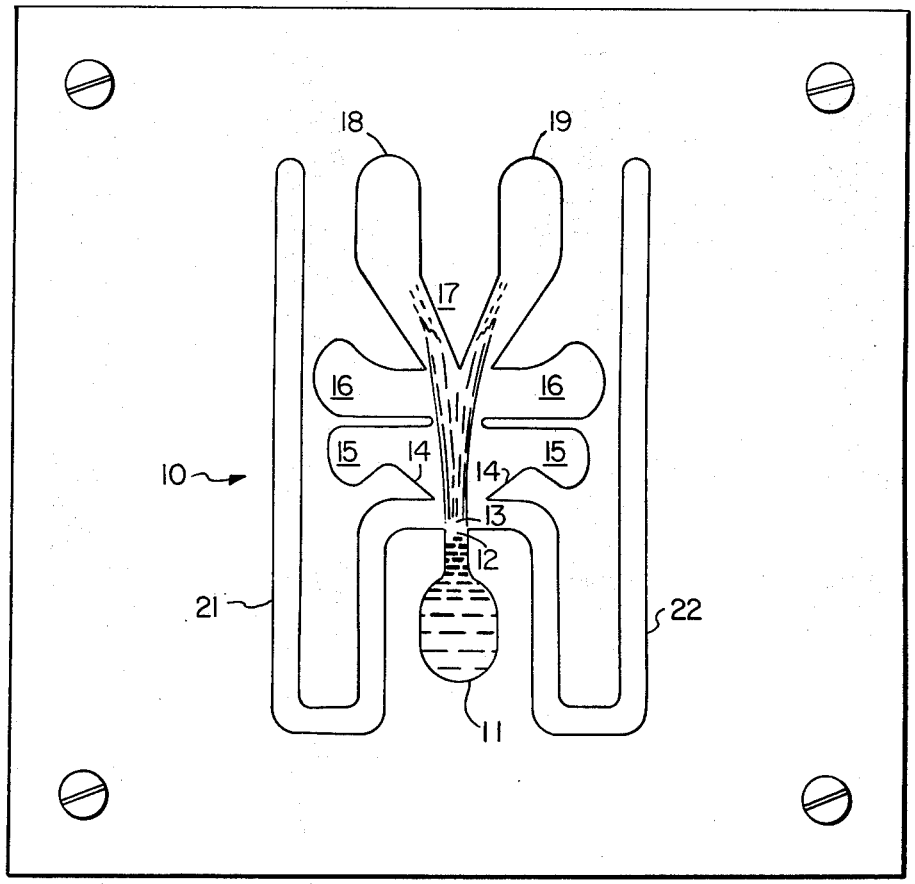

3,952,576

LAMINAR JET FLUID PROPERTY SENSOR

RIGHTS OF THE GOVERNMENT

The invention described herein may be manufactured, used and licensed by or for the United States Government for governmental purposes without the payment to the inventors of any royalty thereon.

BACKGROUND OF THE INVENTION

This invention relates generally to fluidic components and more specifically to a novel way of sensing fluid properties which affect viscosity such as density, temperature, change in fluid constituents and, of course, viscosity itself.

Current concentration sensors have a number of severe and presently unavoidable drawbacks among which are the fact that such concentration sensors are excessively noisy, depend upon elements and/or circuits utilizing moving parts and components, and have a tendency towards rather large sizes and high power consumption.

It is, therefore, a primary object of this invention to provide a device for sensing fluid properties which consists of a single element having no physical moving parts.

A more specific object of this invention is to provide a fluid sensing element which is laminar in operation with a dynamic range in the neighborhood of 5,000 or better.

An additional object is to provide a fluidic sensor of small size and low power consumption.

Still another object of this invention is to provide a fluidic concentration sensor that does not require external or added vacuum sources to draw in a fluid sample.

Yet an additional object is to provide a low output impedance device which readily matches into current technology laminar proportional amplifiers.

These and other objects and aspects of the present invention will become more readily apparent with respect to the following description, the appended claims and the FIGURE which illustrates a planar view of one embodiment of the invention.

SUMMARY OF THE INVENTION

Briefly, in accordance with this invention, a device for sensing fluid properties which affect viscosity comprises a jet of fluid outwardly directed from a nozzle toward a pair of output channels for receiving the fluid. The jet of fluid is controlled by the action of a pair of control channels which control channels are designed such that the channel resistance is equal to the jet edge resistance. More specifically, a reference fluid is placed in one of the control channels and a sample fluid to be tested is placed in the other control channel. Any difference of pressure due to viscosity changes within the two control channels will reflect a change in the direction of the main source of power fluid.

The fluid sensing device is designed as an all laminar single element fluid property sensor which is sensitive to change in resistance of a channel in proportion to a change in fluid property which in turn causes deflection of the laminar fluid jet. The jet deflection is then transduced to an output pressure which is a function of the changed fluid property.

DESCRIPTION OF THE PREFERRED EMBODIMENT

Referring now to the FIGURE, the all laminar fluid sensing device comprises a source of primary fluid 11 which exits from nozzle 12 as a laminar stream 13. The stream divides at splitter 17 and flows into either of output channels 18 or 19 depending upon the deflection action caused by control channels 21 and 22. It is noted that the control channels are unusually long for a fluidic device and are oriented perpendicularly with respect to the stream 13. More specifically, the control channels are designed to have a resistance equal to the jet edge resistance and are approximately 70 times the width of the nozzle 12.

Vent sources 15 and 16 are located downstream of the fluid stream in the usual and well known manner for such devices.

The space between the jet 13 and the edge of the channel 14 acts as a constant value resistor independent of the channel conditions $R_t$. The channel resistance is $R_c$ and is proportional to the fluid viscosity. A difference in resistance of the channel on one side to the other causes a pressure difference across the jet and so deflects it.

This difference in resistance may be effected by introducing a different fluid or fluid temp. etc. on one side (e.g. changing the viscosity). The deflection of the jet may be sensed by placing two channels 18 and 19 along the jet axis and downstream so that when the jet deflects more is impinging on one channel than on another and a differential output, pressure, flow or power, signal may be drawn off. This is not the only way. The jet deflection may be sensed electrically with hot-wire aneomometer, or a miniature pressure sensor, or even mechanically with a rotating vane, or small spring loaded lever arm or any other device. For pure fluid operation the preferred way is to use two output channels as described above.

The output pressure of an all fluid sensor is then determined by making a flow balance on each side of the jet and calculating the difference in jet edge pressure. The output pressure is then merely a constant $G_p$ usually greater than 1 times this difference pressure. Hence for a device where the channel resistance equals the edge resistance the output is:

$$\Delta P_o = G_p \, \gamma \, \frac{\Delta R}{R}$$

where $\gamma = \dfrac{(P_1 - P_d) - R_{ref} Q_e}{\left[4 + \dfrac{2}{R}\left(\dfrac{\Delta R}{R}\right)\right]\left[1 - \dfrac{Ra_1 K_j}{2}\left(\dfrac{\Delta R}{R}\right)\right]}$ $P_1 - P_d$ = pressure difference between channel start and downstream of the jet-edge space $R_{ref}$ = value of resistance when jet is undeflected or there is no signal $Q_e$ = flow entrained by the jet over the width of the channel $\Delta R/R$ = change in channel resistance $a_1$ = difference in net entrainment on either side of the jet due to jet deflection $K_j = ((b_c/b_s)^2/\Delta c_\theta) \, b_s/P_s$ = jet deflection parameter Since $(\Delta R/R)$ can be related easily to changes in viscosity and any parameter affecting viscosity hence the output of such a sensor is directly related to the parameter or property through the appropriate functional relationship.

For example the resistance is proportional to the viscosity.

$$R = \text{Const} \cdot \mu$$

hence $\Delta P_o = G_p \gamma (\Delta \mu / \mu)$ or a differential viscometer. Knowing the viscosity of one constituent also gives an absolute viscosimeter output for the value of an unknown fluid against a known.

The viscosity is a function of temperature hence the device can be a differential or an absolute thermometer. If $$\mu = \mu_o + k T$$

then $$\Delta P_o = \frac{G_p \gamma k \Delta T}{\mu_o} \text{ or } \frac{G_p \gamma k (T_x - T_o)}{\mu_o}$$

The viscosity is also a function of gas density, so when the temperature is held constant and an unknown gaseous mixture is put in through one port and a known reference gas through the other, the output of the sensor will designate the change or the absolute value of the mixed gas. Assuming again for the sake of simplicity a linear relation for viscosity as a function of density $\mu = \mu_o + k_1 \rho$ then the output of the sensor will be $$\Delta P_o = \frac{G_p \gamma k_1}{\mu_o} \Delta \rho$$

The volume fraction of a mix in gas, the concentration, may also be obtained by noting that for two ideal gases the ratio of the mixture viscosity to reference viscosity is $$\frac{\mu_m}{\mu_1} = \frac{1}{1 + \frac{X_2}{1 - X_2} \frac{(1 + \psi^{1/4})^2}{2\sqrt{2}\left(1 + \frac{1}{Z}\right)^{1/2}}} + \frac{1}{1 + \frac{1 - X_2}{X_2} \frac{\left(1 + \frac{1}{\psi^{1/2}}\right)^2}{2\sqrt{2}(1+Z)^{1/2}}}$$

where $$\psi = \frac{(\rho_2/\rho_1)}{(\mu_2/\mu_1)^2} \epsilon \quad Z = \rho_2/\rho_1$$

and $X_2$ is the volume fraction of gas 2. Thus using the viscosimeter principle where $$\Delta P_o = G_p \gamma \frac{\Delta \mu}{\mu} = G_p \gamma \frac{(\mu_m - \mu)}{\mu}$$

or $$\Delta P_o = G_p \gamma \left(\frac{\mu_m}{\mu} - 1\right)$$

so that $$\frac{\mu_m}{\mu} = \frac{\Delta P_o}{G_p \gamma} + 1$$

Substituting and solving for the volume fraction $X_2$ results in $$X_2 = \frac{1}{\frac{\xi \sqrt{\psi z}}{2} + \sqrt{\frac{\xi^2 \psi z}{4} - \sqrt{\psi z} + 1}}$$

where $$\xi = \frac{2AG_p\gamma}{B \Delta P_o} - \left(1 + \frac{G_p\gamma}{\Delta P_o}\right)\frac{A}{B} - \left(1 + \frac{B^2}{A^2} \frac{1}{\sqrt{\psi z}}\right)$$

$$A = 2\sqrt{2}\left(1 + \frac{1}{z}\right)^{1/2}$$

$$B = (1 + \psi^{1/4})^2$$

This equation relates the volume fraction of a constituent gas in a mixture of two gases to the output pressure of the laminar jet sensor.

It should be noted that the jet sensor not have a pressure differential $(P_1 - P_d)$ between the start of the channel and downstream of the jet-edge space. Even if $(P_1 - P_d)$ is zero $\gamma$ is not zero. Flow is drawn through the resistors by the entrainment potential of the jet, and consequently it is not necessary to provide external forcing pressures or vacuum other than to power the supply jet itself.

The foregoing described device makes possible a number of distinct advantages over present devices. These include noise free all laminar operation with a dynamic range in the neighborhood of 5,000 or better; small size for $b_s$ equal to 0.25 mm. The external dimensions can be held to 15 mm × 15 mm × 4 mm; and low power consumption in the vicinity of 0.1 to 4 milliwatts.

In a typical embodiment of the device, the control channels are about 70 $b_s$ in order to make the channel resistance equal to the jet edge resistance. The outputs are designed to have an average width of 3 $b_s$, a length of 20 $b_s$, and a receiver width of 1.5 $b_s$.

From the foregoing it is apparent that we have described a novel all laminar single element fluid property sensor which utilizes the change in resistance of a channel to effect a deflection of a laminar jet. It should be understood that the inventors do not desire to be limited to the exact details of construction shown and described, for obvious modifications can be made by a person skilled in the art.

We claim as our invention:

1. A laminar fluidic device for sensing fluid properties that affect viscosity, said device comprising: a source of supply for directing a jet of fluid outwardly from a nozzle; a pair of control channel means disposed on opposite sides of said jet of fluid for deflecting said jet in response to a difference in the resistance of one control channel means with respect to the other control channel means, said resistance difference effecting a pressure differential across said jet; a pair of output chanels for receiving said jet of fluid in accordance with the deflection thereof; vent means disposed between said nozzle and said output channels; and wherein each said control channel means normally exhibits a channel resistence equal to the jet edge resistence.

2. The device as defined in claim 1, wherein the length of each said control channel means is approximately seventy times the width of said nozzle to effect said normal channel resistence equal to the jet edge resistence.

3. The device of claim 2, wherein said pair of control channel means further respectively contain a reference fluid, and a sample fluid.

4. The device of claim 1, wherein each said control channel means is perpendicularly oriented with respect to said nozzle at the point of intersection.

* * * * *